(12) United States Patent
Mandpe

(10) Patent No.: US 8,197,552 B2
(45) Date of Patent: Jun. 12, 2012

(54) EUSTACHIAN TUBE DEVICE AND METHOD

(76) Inventor: Aditi H. Mandpe, San Francisco, CA (US)

(*) Notice: Subject to any disclaimer, the term of this patent is extended or adjusted under 35 U.S.C. 154(b) by 9 days.

(21) Appl. No.: 12/901,932

(22) Filed: Oct. 11, 2010

(65) Prior Publication Data

US 2011/0028986 A1    Feb. 3, 2011

Related U.S. Application Data

(62) Division of application No. 11/678,919, filed on Feb. 26, 2007, now Pat. No. 7,833,282.

(60) Provisional application No. 60/767,020, filed on Feb. 27, 2006.

(51) Int. Cl.
*A61F 2/04* (2006.01)
*A61F 11/00* (2006.01)
*A61M 5/00* (2006.01)

(52) U.S. Cl. ............ 623/23.7; 604/8; 606/108; 606/109

(58) Field of Classification Search ............... 623/10, 623/23.7; 604/8; 606/108–109
See application file for complete search history.

(56) References Cited

U.S. PATENT DOCUMENTS

2006/0198869 A1* 9/2006 Furst et al. .......... 424/426
2006/0206189 A1* 9/2006 Furst et al. .......... 623/1.11

* cited by examiner

*Primary Examiner* — David Isabella
*Assistant Examiner* — Andrew Iwamaye
(74) *Attorney, Agent, or Firm* — Louis L. Wu

(57) ABSTRACT

Devices are provided for insertion into a Eustachian tube of an animal, e.g., a human being. The devices include an insertable member. The member has opposing surfaces and is formed at least in part from a biocompatible material that is degradable. The device may comprise a hole that is effective to provide sufficient fluid communication between the opposing surfaces of the insertable member to effect pressure equilibration therebetween. The device is able to be immobilized within the Eustachian tube for a predetermined period. Also provided are kits that include the device and methods for inserting the device into a Eustachian tube.

24 Claims, 3 Drawing Sheets

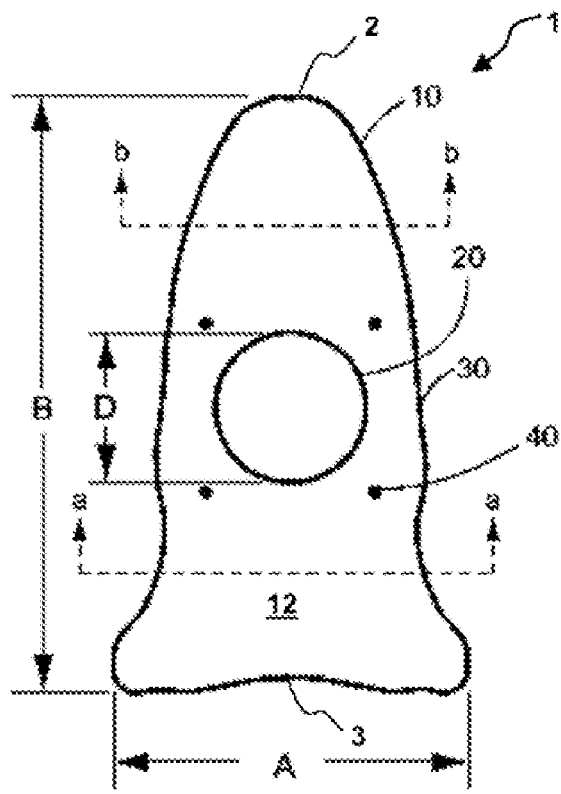
FIG. 1
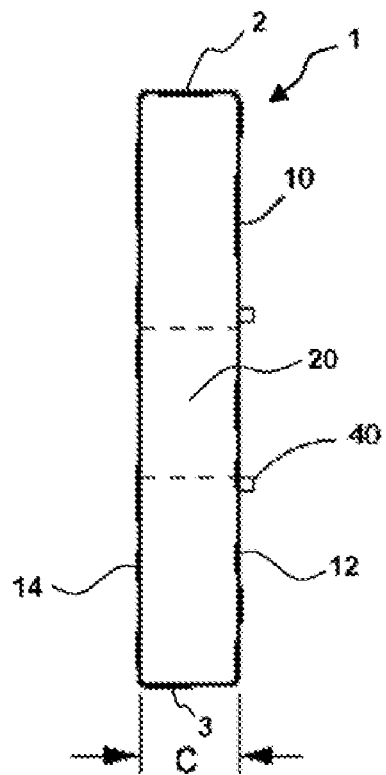
FIG. 2
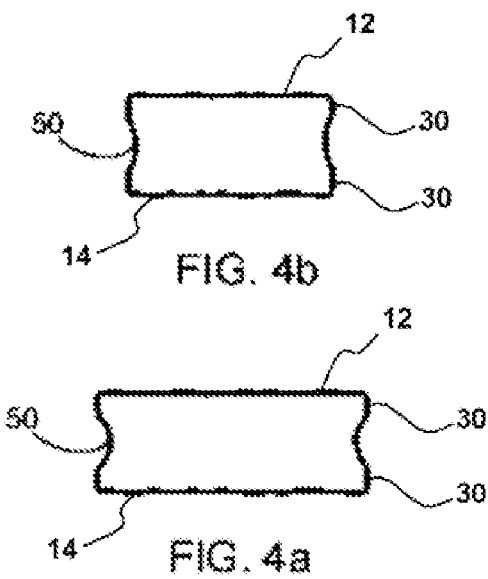
FIG. 4b
FIG. 4a
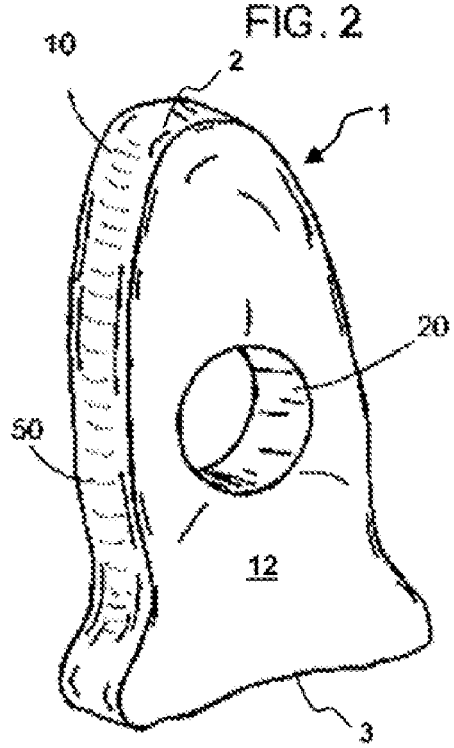
FIG. 3

EUSTACHIAN TUBE DEVICE AND METHOD

CROSS REFERENCE TO RELATED APPLICATIONS

This application is a divisional of U.S. patent application Ser. No. 11/678,919, entitled "Eustachian Tube Device and Method," filed on Feb. 26, 2007, by inventor Aditi H. Mandpe, now U.S. Pat. No. 7,833,282 B2, which claims priority to U.S. Provisional Patent Application Ser. No. 60/767,020, entitled "Eustachian Tube Dilator and Stent," filed on Feb. 27, 2006, by inventor Aditi H. Mandpe, the disclosures of which are incorporated by reference in their entirety.

BACKGROUND

1. Technical Field

The invention generally relates to devices for insertion into a Eustachian tube. In particular, the invention relates to devices that include an insertable member, a means for immobilizing the device, a means for providing sufficient fluid communication between opposing surfaces of the insertable member to effect pressure equilibration therebetween, and to methods for using such devices.

2. Background Art

The Eustachian tube is a hollow lined tube that connects a middle ear to the nasopharynx. The middle ear portion of the tube can only be accessed by incising the eardrum or ear canal skin. The nasal portion of the tube is surrounded by cartilage that regulates opening and closing actions (torus tubarius). In its resting state, the Eustachian tube is in the closed position. Eustachian tube opening action is mediated by contraction of surrounding muscles that impinge upon the tube and torus tubarius. An opened tube ventilates and drains the middle ear and maintains proper pressure relationships among the eardrum, middle ear, and nasopharynx.

Eustachian tube dysfunction has been implicated in the development of various otologic diseases. The etiology of acute otitis media is hypothesized to be due to bacteria traveling into the middle ear from the nasal cavity in a setting of inflammation, which prevents the middle ear from draining properly. Chronic otitis media occurs when the Eustachian tube fails to ventilate the middle ear over an extended period. In these cases, fluid and thickened mucosa accumulate in the middle ear, causing hearing loss. As difficulty ventilating the middle ear continues, skin may become entrapped (cholesteatoma), and cause chronic infection and destruction of the ossicles, inner ear and mastoid air cell system.

Eustachian tube dysfunction is especially problematic for patients who are unable to clear their ears when flying and diving. In the setting of rapidly changing barometric conditions, as in flying and diving, inability to ventilate the middle ear sufficiently can lead to barotrauma with accumulation of fluid or blood in the middle ear. On occasion, Eustachian tube dysfunction patients can experience eardrum rupture, deep hearing loss and dizziness.

Treatment of Eustachian tube dysfunction has mainly been directed at ventilation of the middle ear via the eardrum or tympanic membrane. Typically, a myringotomy or incision through the substance of the eardrum is created, and a ventilation tube is placed within the incision. These ventilation tubes or grommets have been commercially available for over 50 years.

Such treatments are associated with numerous drawbacks. For example, ventilation tubes are typically spontaneous and uncontrollably extruded from the eardrum about 4-9 months after placement. The invasiveness of surgical procedures to the eardrum or tympanic membrane also represents a potential source of complications Some long-term solutions have been proposed. U.S. Pat. No. 3,807,409 to Paparella et al. and U.S. Pat. No. 4,695,275 to Bruce et al. describe eardrum-based methods and modified ventilation tube flanges to promote lengthier tube retention periods. U.S. Pat. No. 3,982,545 to Silverstein and U.S. Pat. No. 5,047,053 to Jahn describe methods of ventilation tube insertion by modifying the ear canal. The materials used for ventilation tube construction for U.S. Pat. No. 3,982,545 is silicone and U.S. Pat. No. 5,047,053 is biointegratable hydroxyapatite. These prostheses may be extruded at variable times and require complex office or operating room procedures to clear debris that surrounds the ventilation tubes.

Direct stenting of the Eustachian tube through the middle ear orifice have been proposed. Devices for carrying out such Eustachian tube stenting have been described, for example, in U.S. Pat. No. 4,015,607 to Wright, III, U.S. Pat. No. 6,589,286 to Litner and PCT/JP2005/020014. As a short-term solution, Litner describes an elongated, drug-eluting stent designed to be secured at the tympanic orifice as a short-term solution to maintain the patency of the Eustachian tube. In contrast, the Wright apparatus is designed as a long-term solution. Long-term Eustachian tube stenting via the middle ear have resulted in unplanned tube extrusion, mucosal inflammation of the Eustachian tube and blockage. In any case, these apparatuses are placed through either a myringotomy or incision into the ear canal.

Myringotomy can lead to persistent abnormalities with the eardrum. In the pediatric age group where myringotomy with ventilation tube insertion is a common procedure, the most concerning complication is permanent eardrum perforation. When eardrums heal after myringotomy, many are clearly abnormal, such as, formation of retraction pockets, thin atrophic membranes, and tympanosclerosis. The impact of these undesirable changes is hearing loss that ranges from 3-5 decibels (dB). Incision into the ear canal is a more technically complex surgical process. Bleeding in the ear canal and scarring of the eardrum are common outcomes.

While previous methods of relieving Eustachian tube dysfunction and associated problems have been focused on the middle ear component, there is recent indication that treatment at the nasopharynx component is promising. A successful method and apparatus for the treatment of Eustachian tube dysfunction at the torus tubarius location would be free of undesirable outcomes associated with eardrum and ear canal based surgical procedures. Poe et al. (2003), "Laser Eustachian Tuboplasty: A Preliminary Report," LARYNGOSCOPE, 113 (4):583-91, describes a surgical procedure which involves partial excision of the cartilaginous portion of the torus tubarius to increase the opening size. This surgical procedure has been effective in preventing the need to replace ventilation tubes in 70% of patients with chronic otitis media.

A non-surgical device that acts to enlarge the torus tubarius aperture on a temporary basis appears to be effective in chronic otititis media. The EarPopper™ delivers a pressure controlled constant volume velocity of air through the nose to the Eustachian tube orifice in the nasopharynx. As disclosed in Arick et al. (2005), "Nonsurgical home treatment of middle ear effusion and associate hearing loss in children. Part I: Clinical trial," EAR, NOSE, THROAT JOURNAL, 85(10):1-13, such a device has been used to restore hearing to normal in 85% of patients without antibiotics or ventilation tubes over 7 weeks.

Nevertheless, opportunities exist to overcome disadvantages associated with known technologies associated with the treatment of disorders associated with an obstructed Eustachian tube.

SUMMARY

In a first embodiment, a device is provided for insertion into a Eustachian tube of an animal, e.g., a human. The device includes, in some instances consists essentially of, an insertable member, an immobilizing means and a fluid-communication providing means. The member has opposing surfaces and is formed at least in part from a biocompatible material that is degradable in the Eustachian tube at a predetermined degradation rate. The fluid-communication providing means is effective to provide sufficient fluid communication between the opposing surfaces of the insertable member to effect pressure equilibration therebetween. The immobilizing means is effective to immobilize the device within the Eustachian tube, typically at a location closer to a nasopharynx than an eardrum, for a predetermined period of time that corresponds to the predetermined degradation rate.

Typically, the predetermined period is selected to allow Eustachian tube function to be restored without having trauma to the Eustachian tube mucosa that potentially may lead to scarring. For example, the immobilization means may have a construction such that degradation of the biocompatible material of the device after the predetermined period within the Eustachian tube leads to a substantially complete extraction of the member from the Eustachian tube. Such extraction may be carried out with or without surgical intervention.

Member geometry may vary. Typically, at least one opposing exterior surface is associated with a member length and member width and the peripheral surface is associated a member thickness such that the member length is greater than the member thickness. In some instances, the member may have a geometry effective to allow the peripheral surface of the member to engage a surface of the Eustachian tube, thereby substantially immobilizing the device within the Eustachian tube upon insertion therein. In such a case, at least one exterior surface may have a substantially triangular shape that corresponds to a cross sectional area of the Eustachian tube. Optionally, the member geometry may exhibit mirror symmetry. In addition, the fluid-communication-providing means may include or consist essentially of a hole extending through the member between the opposing exterior surfaces, the hole being substantially dimensionally stable for at least the predetermined period after the device is inserted into the Eustachian tube.

The device may be provided in a kit that also includes an insertion apparatus, e.g., a spring-loaded hand-held endoscopic apparatus, in an optional container with optional instructions for using the apparatus. The insertion apparatus may be releasably engageable with the device. For example, the device may be constructed to engage the device via the fluid-communication-providing means.

In another embodiment, a method is for inserting a device into a Eustachian tube of an animal. The device may be inserted, using an optionally insertion apparatus, through a nostril or mouth of the animal into the Eustachian tube. The device may then be released manner effective to allow the device to immobilize itself within the Eustachian tube.

BRIEF DESCRIPTION OF THE DRAWINGS

FIG. 1 depicts in front view an exemplary device of the invention in the form of a Eustachian tube dilator and stent.

FIG. 2 depicts in side view the device shown in FIG. 1.

FIG. 3 shows in perspective view of the device shown in FIG. 1.

FIGS. 4a and 4b, collectively referred to as FIG. 4, show cross sectional views near the bottom and top, respectively, of the device shown in FIG. 1.

DETAILED DESCRIPTION OF THE INVENTION

Definitions and Overview

Figure 5:
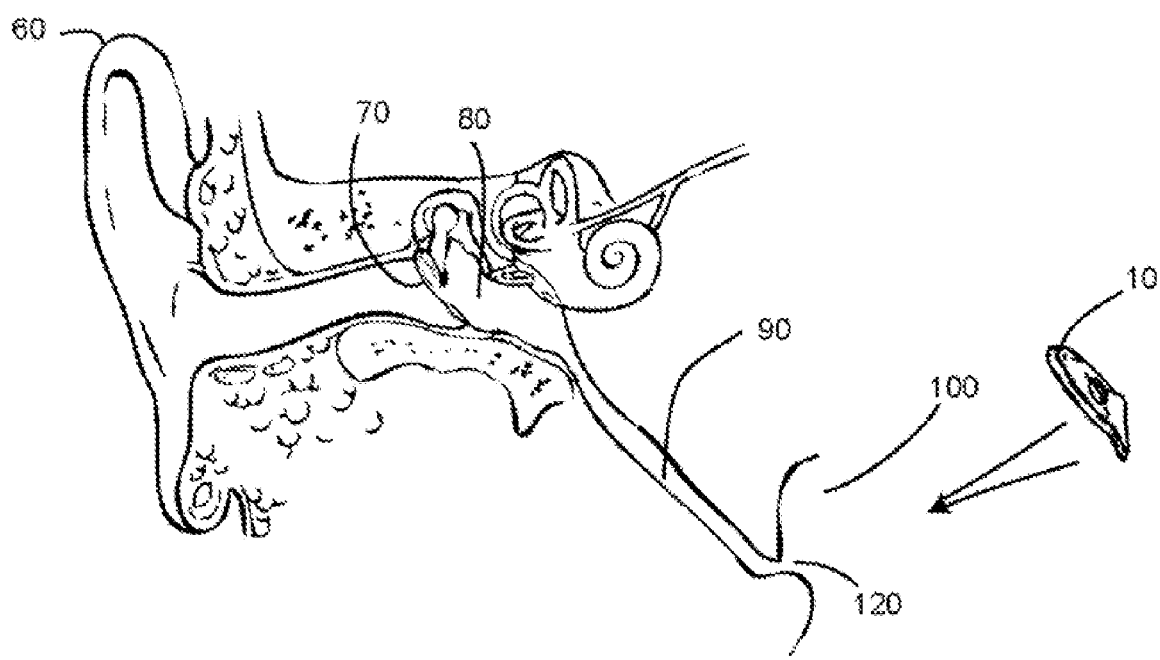
FIG. 5 depicts the placement of the device of FIG. 1 in position in the Eustachian tube at the torus tubarius.
Figure 6:
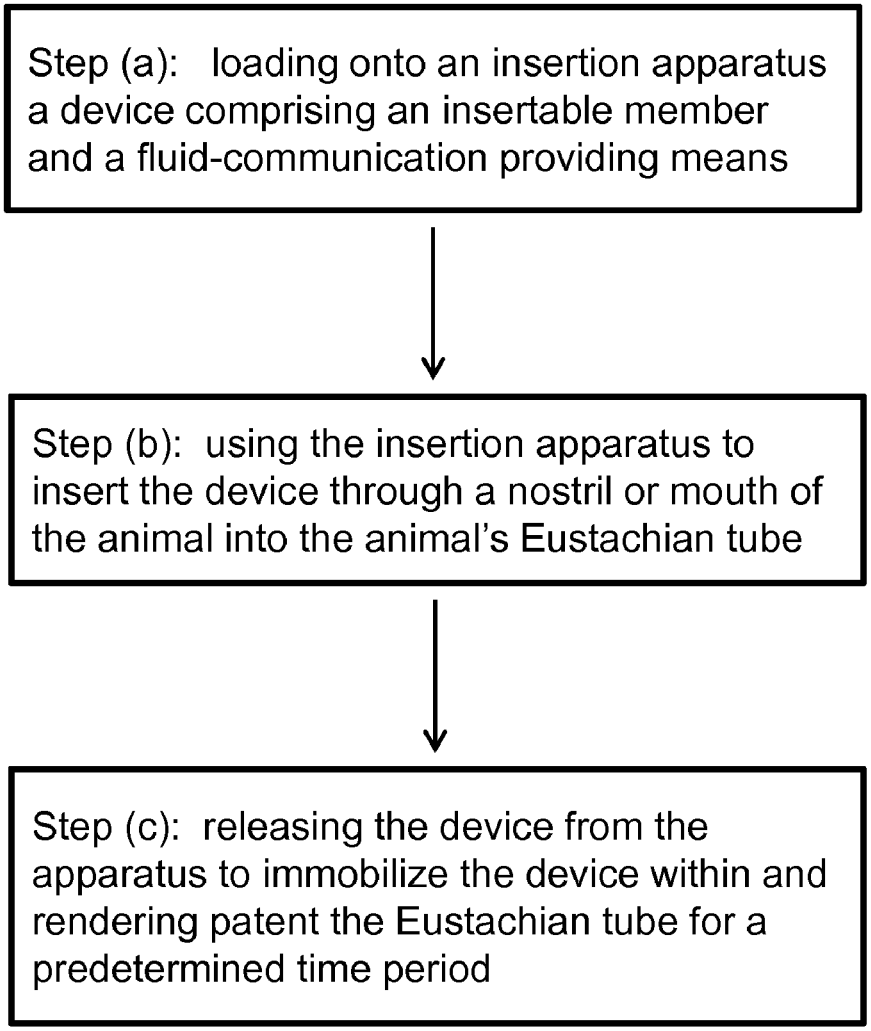
FIG. 6 is a flow chart that shows various steps of an exemplary embodiment of the inventive method.

Before describing the present invention in detail, it is to be understood that the invention is not limited to devices and methods that provide pressure equilibration in any specific manner, for particular fluids and/or for treatment any specific disorders, as such may vary. It is also to be understood that the terminology used herein is for the purpose of describing particular embodiments only, and is not intended to be limiting.

In addition, as used in this specification and the appended claims, the singular article forms "a," "an," and "the" include both singular and plural referents unless the context clearly dictates otherwise. Thus, for example, reference to "an apparatus" includes a single apparatus as well as an assembly of apparatuses, reference to "a hole" includes a plurality of holes as well as a single hole, and reference to "a material" includes a single material as well as a combination of materials, and the like.

In this specification and in the claims that follow, reference will be made to a number of terms that shall be defined to have the following meanings, unless the context in which they are employed clearly indicates otherwise:

The term "biocompatible" refers to the ability of the compositions of the present invention to be applied to tissues without eliciting significant inflammation, fibrosis, or tissue responses that are toxic, injurious or otherwise adverse.

The term "fluid" as used herein in its ordinary sense and refers to an at least partially gaseous and/or liquid substance that easily changes its shape. A fluid may contain a solid that is minimally, partially, or fully solvated, dispersed, or suspended. Examples of fluids include, without limitation, gases (such as oxygen, nitrogen, carbon dioxide, water vapor, and mixtures such as air), aqueous liquids (including water per se, salt water, and physiologic saline solutions), nonaqueous liquids (such as organic solvents, oils and the like), fluid emulsions, suspensions, and/or solutions such as mucus, blood, plasma, lymph, interstitial fluids, etc.

Accordingly, the term "fluid-communication," unless the context of its usage clearly indicates to the contrary, generally encompasses terms such as "air-communication," and "mucus-communication."

"Optional" or "optionally" means that the subsequently described circumstance may or may not occur, so that the description includes instances where the circumstance occurs and instances where it does not.

The term "polymer" and "polymeric" refer to a molecule consisting of individual chemical moieties, which may be the same or different, but are preferably the same, that are joined together. As used herein, the term "polymer" refers to individual chemical moieties that are joined end-to-end to form a linear molecule, as well as individual chemical moieties joined together in the form of a branched structure.

The term "resorbable" is used herein in its ordinary sense and describes a degradable material that can be both dissolved in and biologically assimilated by a patient.

The terms "substantial" and "substantially" are referred to herein in their ordinary sense and are used to describe matters that are, e.g., considerable in importance, value, degree, amount, and/or extent. For example, a device that is "substantially immobilized" in the Eustachian tube is neither required nor precluded from absolute immobilization as long as movability of the device in the Eustachian tube is reduced to a generally trivial degree that does not compromise the intended functionality of the device within the Eustachian tube. Other uses of the term "substantially" involve an analogous definition.

In general, the invention pertains to devices, apparatus and method for inserting a device into a Eustachian tube of an animal. Typically, the device is used to dilate, provide mechanical support, and/or stent the Eustachian tube at location closer to a nasopharynx than an eardrum, e.g., the torus tubarius orifice, which in turn, maintains patency of the Eustachian tube. The method of placement of the apparatus is via the nasal and/or oral passages and nasopharyngeal opening of the Eustachian tube and does not require incision of the eardrum, ear canal or entry into the middle ear.

In some instances, the device includes an insertable member, an immobilizing means and a fluid-communication providing means. The member has opposing surfaces and is formed at least in part from a biocompatible material that is degradable in the Eustachian tube at a predetermined degradation rate. The fluid-communication providing means is effective to provide sufficient fluid communication between the opposing surfaces of the insertable member to effect pressure equilibration therebetween.

The construction of the inventive device may vary depending on the functionality desired. As an initial matter, the device should be constructed according to the physiology of the animal into whose Eustachian tube is intended to receive. As the invention may be used for any animal having a Eustachian tube, the invention may be constructed for humans (e.g., patients who are infants, children, teenagers, adults, and seniors), domesticated animals such as dogs, cats, horses, cattle, and pigs, and nondomesticated animals.

The predetermined rate may be selected according to a plurality of selection criteria, singly and in combination. For example, when the device is constructed to treat a disorder associated with the Eustachian tube, the rate may be chosen to ensure restoration of proper Eustachian tube function within a predetermined period without having trauma to the Eustachian tube mucosa that potentially may lead to scarring. In some instances, the predetermined rate may correspond to a predetermined period of about 2-8 weeks to allow fluid to sufficiently drain from an acute infection and allow the Eustachian tube function to be restored. In some instances, the predetermined period may be closer to about 2-3 weeks. In addition, once the tube is properly functioning, keeping the opening stented for an excessive time period may lead to an unexpected problem with an echo in the ear while speaking. Accordingly, the predetermined period typically does not exceed about one year. On occasion, the device may be surgically removed.

When placed in the Eustachian tube at the torus tubarius, e.g., through a minimally invasive procedure that results in device placement through the nasal passages or through the oropharynx under the palate, the device confers a number of advantages previously unknown in the art. For example, the benefits of a nasopharyngeal-based therapy may be achieved without the disadvantages of the undesirable outcomes associated with treatment methods that involve an incision in the ear canal or eardrum, or entry into the middle ear space. In addition, such placement of the device in the Eustachian tube may provide immediate relief from fluid in the ear and pressure related maladies.

As the device renders the Eustachian tube patent, the device may aerate the middle ear, become a portal to drain fluid and infection from the middle ear, treat retracted eardrums and ear congestion, and prevent pressure related damage to the ear associated with activities such as, airplane travel, diving, and high altitude activities. The device may also enable diagnostic microendoscopy of Eustachian tube and the middle ear, and serve as a conduit for the diagnosis and assessment of middle and inner ear functions, integrity of the ossicles, chronic ear infection and cholesteatoma. Further, the device may serve as a stent and protective dressing for any hard and soft palate, nasopharyngeal, or Eustachian tube surgery.

An Exemplary Device

The invention provides, in an exemplary embodiment, a device constructed from biocompatible and bioresorbable implantable materials with biomechanical properties that provide opening forces necessary to keep the Eustachian tube orifice patent. The device includes an insertable member that has a triangular shaped arch with a central opening that dilates and stents the Eustachian tube, and ventilates the middle ear. The insertable member has a contoured lip that allows the device to be snapped into position at the nasopharyngeal orifice of the Eustachian tube. The device has structural memory to maintain its shape and a central hole to ventilate the middle ear.

FIGS. 1-4 show such an embodiment of the invention in the form of a device 1 that may serve as Eustachian tube dilator and stent for a human patient. As is the case with all figures referenced herein, in which like parts are referenced by like numerals, FIGS. 1-4 are not necessarily to scale, and certain dimensions may be exaggerated for clarity of presentation. As shown in FIG. 1, the device 1 includes an insertable member 10 having a first exterior major surface 12 having a shape generally corresponding to an acute isosceles. Such a shape also generally corresponds to the cross sectional area of the torus tubarius opening for a Eustachian tube of an ordinary human patient. The device has a width indicated by A, which corresponds to the widest dimension of the member's bottom end 3. Width A may range from about 3 mm to about 8 mm, but is typically about 5 mm. As shown, the bottom portion of the device exhibits a generally flanged geometry. The device has a length indicated by B, which corresponds to the distance between the top end 2 and the bottom end 3 of the member 10. Length B may extend about 6 mm to about 12 mm, but is typically about 9 mm.

FIG. 2 depicts the device of FIG. 1 in side view. As shown in FIG. 2, the device also has a second major exterior surface 14. Surfaces 12 and 14 are both planar, have a substantially identical shape, and are parallel to each other. The thickness of the device is generally uniform and indicated by C, which represents the distance between surfaces 12 and 14. Though thickness C may range from about 2 mm to about 4 mm, C is typically about 2 mm.

As shown in FIGS. 1 and 2, a central ventilating hole 20 having a generally circular shape serves as a means for providing fluid communication between major surfaces 12 and 14. Hole 20 has a diameter D that is typically about 3 mm, but may range from about 2 mm to about 4 mm. The dotted lines of FIG. 2 represent side walls of the hole 20 carried from FIG. 1 and serves to indicate the upper and lower extent of the central ventilation hole 20. As shown, the hole 20 extends in a substantially perpendicular orientation relative to surfaces 12 and 14. Four optional protrusions 40 extend from first surface 12 and may serve as insertion flanges.

The overall geometry of the device 1 in perspective view is represented in FIG. 3. As shown, the device member 10 has a triangular arched shaped structure with the central ventilating hole 20. The first surface 12 and the second surface (not shown) are connected by a peripheral surface 50, which generally encircle the device 1.

FIG. 4 represents cross-sectional views of the device along a-a and b-b lines in FIG. 1. As shown in FIG. 4, the peripheral surface 50 takes the form of a concave groove bounded by contoured lips 30. In some instances, contoured lips 30 start from one lateral aspect of device 1 near its bottom 3, cross the top 2 and terminate at the corresponding opposing lateral aspect of the device 1. The groove and lip construction may serve as a means for immobilizing the device.

FIG. 5 shows the device 1 in context with for proper positioning in the torus tubarius 120 of a human patient to achieve Eustachian tube patency. FIG. 5 contains a cross-sectional representation of the ear along the external auditory canal and length of the Eustachian tube 90. The external ear or pinna 60 is the most lateral structure. The eardrum 70 and middle ear space 80 are not violated in the insertion process. The Eustachian tube orifice or torus tubarius 120 resides within the nasopharynx 100. When the device 1 is properly positioned, the lips 30 and groove 50 allows the device 1 to be snapped into the anterior and posterior lips of the torus tubarius 120.

Device Geometry and Construction

As discussed above, device geometry and construction may vary according to its functionality. In general, the device includes or consists essentially of an insertable member, an immobilizing means and a fluid-communication providing means. The member has opposing surfaces and is formed at least in part from a biocompatible material. The fluid-communication providing means is effective to provide sufficient fluid communication between the opposing surfaces of the insertable member to effect pressure equilibration therebetween.

The opposing surfaces may be connected by a peripheral surface. Typically, at least one of the opposing surfaces represents a major surface of the member. In such a case, the major surface is associated with a member length and member width and the peripheral surface is associated a member thickness. In addition, at least one exterior major surface may have a shape that substantially corresponds to a cross sectional area of the Eustachian tube. Though surfaces of the invention may be generally smooth, it may be possible to produce devices such that any surface may have any desired contour, e.g., jagged, undulated, etc.

A number of optional features may be incorporated into the construction of the inventive device to address certain manufacturing and/or functionality concerns. For example, to facilitate ease in manufacturing, the opposing surfaces may be rendered substantially planar and parallel to each other. As a result, the insertable member may have a uniform thickness. In the alternative, the device may assume a gentle curvilinear contour in the front to back and top to bottom dimensions and have a non-uniform thickness profile.

The member length is typically greater than the member thickness. Typically, the device length exceeds the thickness by at least 50%. In some instance, the device width is greater than the thickness as well. In any case, when a device is constructed for insertion into the Eustachian tube for either ear, left or right, the device may have a member geometry that exhibits mirror symmetry.

Typically, the member and the immobilization means have an integrated construction. For example, the member may have a geometry effective to allow the peripheral surface of the member to engage a surface of the Eustachian tube, thereby substantially immobilizing the device within the Eustachian tube upon insertion therein. In such a case, the device may have mechanical properties that provide forces necessary to render the device immobile, e.g., the member may be at least partially elastically deformable before immobilization. Optionally, the insertable device itself may be formed from a material compounded with one or more adhesives.

Optionally, nonintegrated immobilization means may be used. For example, adhesives may be used containing compositions that allow the insertable member to become anchored in place by mechanical and/or chemical means. In some instances, an adhesive may be applied as an interfacial composition between the insertable member and the Eustachian tube.

In any case, at least one exterior surface may have a substantially triangular shape that corresponds to a cross sectional area of the Eustachian tube. For example, when the Eustachian tube includes a torus tubarius defined at least in part by anterior and posterior pillars meeting at a top portion of the torus tubarius, the member may exhibit a geometry such that the peripheral surface is effective to engage at least a portion of the torus tubarius so as to immobilize the device in the Eustachian tube. In particular, the member geometry may be effective to allow a vertex portion of the peripheral surface to engage the top portion of the torus tubarius and/or allow side portions of the peripheral surface to engage anterior and posterior pillars of the torus tubaris.

While in some rare instances the inventive device may be considered a permanent implant, the immobilization means is typically be provided in a manner that allows for the device to be engaged with the Eustachian tube temporarily for a predetermined period of time and to be disengaged from the Eustachian tube in a controlled manner. Typically, the immobilization means has a construction such that degradation of the biocompatible material of the device after the predetermined period within the Eustachian tube leads to a substantially complete extraction of the member from the Eustachian tube. Such extraction may be carried out with or without surgical intervention. Typically, the predetermined period corresponds to the predetermined degradation rate of the device material.

As is the case with the immobilization means, the fluid-communication providing means may vary in construction as well. In general, the fluid-communication-providing means may be effective to equilibrate any fluid-generated pressure between the opposing surfaces, regardless whether the pressure is generated from gases and/or liquids. However, in some instances, the fluid-communication providing means may be selective for fluid type. For example, such means may be effective to equilibrate at least partially gas-generated or at least partially liquid generated pressure between the opposing surfaces.

When provided as an integrated component of the insertable member, the fluid-communication providing means extend through any portion of the opposing surfaces so as to allow for pressure equilibration therebetween. In some instances, such means may be centrally located through the member. In the alternative, the means may be eccentric to the top, bottom or side.

In a number of embodiments, the fluid-communication providing means may include or consist essentially of a hole extending through the member between the opposing exterior surfaces. The hole may have any cross-sectional shape, including, for example, circle, oval, square, triangular, hexagonal, etc. For ease in construction, the hole may have a constant cross-sectional area and shape along its length. Similarly, the hole may extend in a substantially perpendicular orientation relative to the opposing surfaces. In any case, the member should have a construction such that a hole, when present as a fluid-communication providing means, is substantially dimensionally stable for at least the predetermined period after insertion into the Eustachian tube. Were the hole to be reduced in size in the Eustachian tube environment, the hole may lose its pressure equilibration functionality.

Device Materials

The inventive device may be formed in part or in whole from a number of materials. Device materials are typically selected so as to ensure optimal device performance given the particular construction and/or geometry of the device. Optionally, the device materials may be tailored to the environmental conditions to which the device may be exposed when inserted into the Eustachian tube. It is expected that the environmental conditions of the Eustachian tube may vary according to a number of factors, e.g., the particular temperature of the animal whose Eustachian is to receive the device, whether the Eustachian tube is healthy or diseased, whether pus or other bodily fluids are present, etc.

In some instances, the insertable member may be substantially uniform in composition. However, the insertable member may be comprised of a plurality of regions that form an integrated whole. For example, the member, in some embodiments, may be comprised of an interior region and a peripheral region, wherein the regions exhibit different compositions. In such a case, at least the peripheral region may be formed from a biocompatible and resorbable or degradable material. The bulk and microstructure of the materials used with the invention should be controlled in order to produce an insertable member of controlled mechanical properties (e.g., tensile strength, elasticity) and resorption properties. In such a case, the dual layer functionality may provide greater control over device performance.

Typically, the insertable member is formed in large part or entirely from a biocompatible and optionally resorbable material that is non-toxic, noninflammatory and nonimmunogenic. The material is typically synthetic or man-made. However, a naturally occurring composition may be used as well. Biocompatibility typically requires a material purity of a pharmaceutically acceptable grade.

Materials for use with the invention may be selected in a manner to provide precise control over device resorption/enzymatic degradation rate. Often, materials are employed comprising one or more hydrophilic compound, mixtures thereof, copolymers of the forgoing, and combinations of the aforementioned. Polymeric materials may be employed because the resorption rate may be established by controlling the molecular weight and/or the degree of crosslinking associated with the polymeric material. Suitable hydrophilic polymers used herein include polyethylene glycol, polyoxyethylene, polymethylene glycol, polytrimethylene glycols, polyvinylpyrrolidones, and derivatives thereof. In some limited instances, polylactic acids may be employed as well. The polymers can be linear or multiply branched and will not be substantially crosslinked. Other suitable polymers include polyoxyethylene-polyoxypropylene block polymers and copolymers. Polyoxyethylene-polyoxypropylene block polymers having an ethylene diamine nucleus (and thus having four ends) are also available and may be used in the practice of the invention.

One suitable material for use in the present invention comprises a polyethylene glycol (PEG) containing compound, due to its known biocompatibility. Various forms of PEG are extensively used in the modification of biologically active molecules because PEG can be formulated to have a wide range of solubilities and because it is low in toxicity, antigenicity, immunogenicity, and does not typically interfere with the enzymatic activities and/or conformations of peptides. Further, PEG monomers are generally non-biodegradable and is easily excreted from most living organisms, including humans. Other synthetic polymeric materials suitable for use include, for example, polyvinyl alcohols, polyacrylic acids, polyglycolic acids, polydioxanones.

In some instances, naturally occurring compounds may be employed to form the insertable member. Suitable naturally occurring compounds include, but are not limited to: polysaccharides such as hyaluronic acid, cyclodextrin, hydroxymethylcellulose, cellulose ether, and starch; glycans such as glycosaminoglycan and proteoglycan; and various proteins.

Proteins such as collagen and other collagenic (collagen-like) materials may be suited for use in the present invention. Collagen, in its native form, is typically a rigid, rod-shaped molecule approximately 300 nm long and 1.5 nm in diameter. It is composed of three collagen polypeptides, which together form a tight triple helix. The collagen polypeptides are each characterized by a long midsection having the repeating sequence —Gly—X—Y—, where X and Y are often proline or hydroxyproline, bounded at each end by the "telopeptide" regions, which constitute less than about 5% of the molecule. The telopeptide regions of the collagen chains are typically responsible for the crosslinking between chains, and for the immunogenicity of the protein, and when removed, may allow collagenic compounds to serve as a biocompatible device member material.

Collagen occurs in several types, having distinct physical properties. Suitable collagenic materials include all types of pharmaceutically useful collagen, e.g., types I, II, and III. Collagens may be fibrillar or non-fibrillar, e.g., methylated or succinylated. In some instances, collagen crosslinked and/or conjugated using heat, radiation, or chemical agents such as glutaraldehyde may be employed.

The invention may be used in conjunction with pharmaceutical technologies known in the art. For example, the device member may include a pharmacologically active constituent. Such constituents may be bound to the device member or may be eludable. Such pharmacologically active constituents may promote post-operative healing and may include, for example, antibiotics, antifungal agent, anti-inflammatory, or the like. In the alternative, the biocompatible material may be free from any pharmacologically active constituents.

The device according to the present invention may be produced in a number of ways. One simple method involves pouring a sterile solution of a precursor member material into a sterile mold cavity to harden. The mold cavity may be composed of stainless steel, elastomeric or thermoplastic tubing, glass, or other substances. Optionally, a releasing agent is interposed between the mold and the solution. While the device member according to the present invention may be cast with a fluid-communication providing means extending the member, the member may be cast solid and bored to produce a hollow communication passage therethrough.

Extrusion may be employed as well to form the inventive device. Most if not all of the above-described materials may be formulated for extrusion through a suitable orifice. Depending on the particular formulation, crosslinking may occur during or after extrusion.

Generally, the microstructure of the materials used with the invention should be controlled in order to produce an insertable member of controlled mechanical properties (e.g., tensile strength, elasticity) and resorption properties. For example, increasing the degree of crosslinking in the member compositions tends to increase the device's tensile strength, rigidity, and resistance to resorption.

Eustachian Tube Methods

In another embodiment, the invention also provides a method for inserting a device into a Eustachian tube of an animal. The method involves inserting the device as described above through a nostril or mouth of the animal into the Eustachian tube. Optionally, the device is inserted solely through the nasopharyngeal opening of the Eustachian tube through the nose or the oropharynx in a manner that does not involve making any incision to an eardrum or ear canal skin. The device may then be released manner effective to allow the device to immobilize itself within the Eustachian tube at its opening in the nasopharynx. The method may be performed with local anesthesia or sedation as appropriate.

Depending on the particulars of the nasal cavity configuration, the device may be inserted into the mouth or whichever nostril that allows for greater ease for device placement in either the right or left Eustachian tube. In particular, the device may be placed through the nasal passages or through the oropharynx under the palate. Advantageously, the method does not require an incision in the ear canal or eardrum, or entry into the middle ear space.

The method may involve the use of an insertion apparatus. For example, the method may involve loading onto an insertion apparatus and using the insertion apparatus to insert the device through a nostril or mouth of the animal into the Eustachian tube. Once the device is in place, the device may be released from the apparatus in a manner effective to allow the device to immobilize itself within the Eustachian tube.

Once the device has been properly positioned and immobilized, the Eustachian tube remains patent. During the device-induced patency of the Eustachian tube, the middle ear is aerated. The device effectively becomes a portal to drain fluid and infection from the middle ear.

The inventive method may be carried out, optionally through endoscopy, in conjunction with surgery or in the absence of any incision. Regardless whether the Eustachian tube into which the device is inserted is surgically unaltered or altered, the method may be effective to dilate the Eustachian tube temporarily or permanently. Furthermore, the method may be effective to prevent collapse of the Eustachian tube and/or involve insertion of the device into an enlarged Eustachian tube.

The inventive method and device may be used to treat certain types of hearing loss, tinnitus, ear discomfort and headache. The method can treat dysfunction of the Eustachian tube due to scarring from surgery, radiation treatment, infection and inflammation affecting the Eustachian tube. The device also enables diagnostic microendoscopy of Eustachian tube and the middle ear, and serves as a conduit for the diagnosis and assessment of middle and inner ear functions, integrity of the ossicles, chronic ear infection and cholesteatoma. Further, the device serves as a stent and protective dressing for any hard and soft palate, nasopharyngeal, or Eustachian tube surgery.

Still further, the invention may be effective to treat retracted eardrums and ear congestion. By dilating and stenting the Eustachian tube, barometric Eustachian tube dysfunction may be treated, and pressure related damage to the ear associated with activities such as, airplane travel, diving, and high altitude activities may be prevented. Allergic and/or infectious Eustachian tube dysfunction may also be treated. Both chronic and acute Eustachian tube dysfunction may be treated.

Insertion Apparatuses and Kits

As discussed above, an insertion apparatus may be used to place the device into and/or extract the device from the Eustachian tube. The insertion apparatus may have any of a number of designs and construction. The insertion apparatus, in some embodiments, is endoscopic and hand held in construction. The apparatus should provide a user sufficient degree of control over the insertion and/or extraction of the device in a minimally invasive manner so as to minimize trauma or discomfort to a patient. Thus, the apparatus may provide for precisely and accurately controlled translational (e.g., X-Y-Z) and/or, rotational ($\theta$-$\phi$) movement capabilities. The apparatus may allow for one, two, three, four, five, six, or more degrees of freedom.

For example, the apparatus may have a device-interfacing terminus and a manipulation terminus. The device-interfacing terminus may have a construction specific to the inventive device or may be used to interface with devices other than those described herein. For example, the interfacing terminus may have a solid or hollow geometry specific to the inventive device. In some instances, the interfacing terminus may also provide for functionality associated with the practice of the inventive method. Exemplary functionality include suction, aspiration, delivery of air or medications to the middle ear.

The manipulation terminus may house a means for releasing any device engaged therewith. The releasing means may have a spring-loaded mechanism, or manual release mechanism that allows the inventive device to be releasably engageable with device-interfacing terminus of the apparatus. Optionally, the device may be controllably slid from the insertion apparatus into the Eustachian tube.

In some instances, the inventive device may be constructed with a means for interfacing with the insertion apparatus. In some instances, such means serve no other purpose than to interface with the insertion apparatus. For example, the interfacing means may include at least one protrusion extending from an exterior surface by which the insertion device may grab. As another example, one or more tabs or fenestrations may be located on either or both front and back surfaces of the device around the fluid-communication providing means.

In the alternative, the interfacing means may serve a plurality of purposes. For example, the fluid-communication providing means may have a construction effective to serve as means for engaging with the insertion apparatus. When a hole is provided as the fluid-communication providing means, the insertion apparatus may be constructed to engage the device via the fluid-communication-providing means through a friction fitting.

As another alternative, the interfacing means may be used to make adjustments to the device to be inserted and/or extracted. For example, the interfacing means may be used to adjust the fluid-communication providing means. When the fluid-communication providing means is in the form of a central hole, the hole may be made smaller or larger through the insertion device. Such sizing may be carried out mechanically and/or remotely. For example, the central hole can be made larger through laser ablation, or, in the alternative, be made smaller through controlled thermal activation or heat regulation.

The device may be packaged with the insertion apparatus to form a kit. Typically, the kit also includes container for containing the insertion apparatus and the device. Optionally, instruction for using the apparatus with the device may be included.

Variations of the present invention will be apparent to those of ordinary skill in the art in view of the disclosure contained herein. For example, while the geometry of the inventive device has been described in detail for use with a living human patient, one of ordinary skill in the art may take measurements from nonhuman animal cadavers to determine the geometry required for such animals. Similarly, while the fluid-communication providing means has been generally described as a single hole extending through the opposing surfaces of the insertable member, such means may include a plurality of holes as well as no holes. Instead, a membrane that is selectively permeable to specific fluids may be used as a fluid-communication providing means. Other variations of the invention may be discovered upon engage in routine experimentation during the ordinary course of the practice of the invention.

It is to be understood that, while the invention has been described in conjunction with the preferred specific embodiments thereof, the foregoing description merely illustrates and does not limit the scope of the invention. Numerous alternatives and equivalents exist which do not depart from the invention set forth above. In general, any particular embodiment of the invention may be modified to include or exclude features of other embodiments. Other aspects, advantages, and modifications within the scope of the invention will be apparent to those skilled in the art to which the invention pertains.

All patents, patent applications, and publications mentioned herein are hereby incorporated by reference in their entireties to an extent not inconsistent with the disclosure provided above.

I claim:

1. A method for inserting a device into a Eustachian tube of an animal, comprising:
   (a) loading a device onto an insertion apparatus, the device comprising an insertable member that is sized for insertion within the Eustachian tube that defines a cross sectional area, the member having a preinsertion form that includes
      opposing exterior surfaces connected by a peripheral surface,
         wherein at least one opposing exterior surface defines a member length and member width, and
         the opposing exterior surfaces define a member thickness such that the member length is greater than the member thickness,
      means for immobilizing the device within the Eustachian tube upon insertion therein, and
      means for providing fluid communication between the opposing surfaces of the member to effect pressure equilibration therebetween;
   (b) using the insertion apparatus to insert the device through a nostril or mouth of the animal into the Eustachian tube; and
   (c) releasing the device from the apparatus in a manner effective to allow the device to immobilize itself within the Eustachian tube while maintaining its preinsertion form, thereby rendering patent the Eustachian tube for a predetermined time period.

2. The method of claim 1, carried out in a manner without incising any ear drum or ear canal skin.

3. The method of claim 1, wherein the animal is human.

4. The method of claim 2, wherein the member is formed at least in part from a biocompatible material that is degradable in the Eustachian tube at a predetermined degradation rate, and the immobilizing means is effective to immobilize the device within the Eustachian tube for the predetermined period of time that corresponds to the predetermined degradation rate.

5. The method of claim 4, wherein the predetermined period is about two to about eight weeks.

6. The method of claim 4, wherein the member is formed entirely from the biocompatible material.

7. The method of claim 4, wherein the member has an interior region and a peripheral region, and the regions comprise different materials.

8. The method of claim 7, wherein the peripheral region is formed from the biocompatible material.

9. The method of claim 4, wherein the biocompatible material is free from any pharmacologically active constituent.

10. The method of claim 4, wherein the biocompatible material includes a pharmacologically active constituent.

11. The method of claim 10, wherein the pharmacologically active constituent is elutable from the biocompatible material.

12. The method of claim 4, wherein the member and the immobilization means have an integrated construction such that the device is at least partially elastically deformable before immobilization.

13. The method of claim 4, wherein the member includes the immobilization means and has a construction such that degradation of the biocompatible material of the device after the predetermined period within the Eustachian tube leads to a substantially complete extraction of the member from the Eustachian tube without surgical intervention.

14. The method of claim 1, wherein the member has a geometry effective to allow the peripheral surface of the member to engage a surface of the Eustachian tube, thereby substantially immobilizing the device within the Eustachian tube upon insertion therein.

15. The method of claim 14, wherein the Eustachian tube includes a torus tubarius defined at least in part by anterior and posterior pillars meeting at a top portion of the torus tubarius, and the member has a geometry such that the peripheral surface is effective to engage at least a portion of the torus tubarius so as to immobilize the device in the Eustachian tube.

16. The method of claim 14, wherein the width is greater than the thickness.

17. The method of claim 14, wherein the length exceeds the thickness by at least 50%.

18. The method of claim 1, wherein the fluid-communication-providing means includes a hole extending through the member between the opposing exterior surfaces.

19. The method of claim 18, wherein the member has a construction such that the hole is substantially dimensionally stable for at least the predetermined period after insertion into the Eustachian tube.

20. The method of claim 1, further comprising (d) extracting the device from the Eustachian tube after the predetermined time period.

21. A method for inserting a device into a Eustachian tube of an animal, comprising:
   (a) loading a device onto an insertion apparatus, the device comprising
      an insertable member that is sized for insertion within the Eustachian tube that defines a cross sectional area, the member having a preinsertion form that includes
         opposing exterior surfaces connected by a peripheral surface, at least one of the exterior surfaces having a triangular shape and size that corresponds to the cross sectional area of the Eustachian tube, and means for providing fluid communication between the opposing surfaces of the member to effect pressure equilibration therebetween;

(b) using the insertion apparatus to insert the device through a nostril or mouth of the animal into the Eustachian tube; and (c) releasing the device from the apparatus in a manner effective to allow the device to immobilize itself within the Eustachian tube, thereby rendering patent the Eustachian tube for a predetermined time period.

22. The method of claim 21, wherein the member has a geometry that exhibits mirror symmetry.

A method for inserting a device into a Eustachian tube of an animal a human, comprising:

(a) loading a device onto an insertion apparatus, the device consisting essentially of an insertable member that is sized for insertion within the Eustachian tube that defines a cross sectional area, the member having a preinsertion form that includes opposing exterior surfaces connected by a peripheral surface, the exterior surfaces each having a triangular shape and size that corresponds to the cross sectional area of the Eustachian tube, and means for providing fluid communication between the opposing surfaces of the member to effect pressure equilibration therebetween;

(b) using the insertion apparatus to insert the device through a nostril or mouth of the animal into the Eustachian tube; and (c) releasing the device from the apparatus in a manner effective to allow the device to immobilize itself within the Eustachian tube, thereby rendering patent the Eustachian tube for a predetermined time period.

23. A method for inserting a device into a Eustachian tube of an animal, comprising:

(a) loading a device onto an insertion apparatus, the device consisting essentially of an insertable member that is sized for insertion within the Eustachian tube that defines a cross sectional area, the member having a preinsertion form that includes opposing exterior surfaces connected by a peripheral surface, the exterior surfaces each having a triangular shape and size that corresponds to the cross sectional area of the Eustachian tube, and means for providing fluid communication between the opposing surfaces of the member to effect pressure equilibration therebetween;

(b) using the insertion apparatus to insert the device through a nostril or mouth of the animal into the Eustachian tube; and (c) releasing the device from the apparatus in a manner effective to allow the device to immobilize itself within the Eustachian tube, thereby rendering patent the Eustachian tube for a predetermined time period.

24. The method of claim 23, wherein the opposing surfaces are substantially planar.

* * * * *